United States Patent [19]

Raychok, Jr. et al.

[11] Patent Number: 4,600,618
[45] Date of Patent: Jul. 15, 1986

[54] SPLINT MATERIAL WITH HOOK AND LOOP FASTENER

[76] Inventors: Paul G. Raychok, Jr., 6953 Clock Gate, Troy, Mich. 48098; Linda K. Katt, 604 Fox River Dr., Bloomfield Hills, Mich. 48013

[21] Appl. No.: 591,399

[22] Filed: Mar. 16, 1984

[51] Int. Cl.$^4$ .............................................. A61F 5/04
[52] U.S. Cl. .................................... 428/92; 128/90; 428/95; 428/100
[58] Field of Search ................... 428/92, 95, 100; 128/90

[56] References Cited

U.S. PATENT DOCUMENTS 3,667,462  6/1972  Moon ................... 428/100
4,215,687  8/1980  Shaw ................... 428/100

Primary Examiner—Marion C. McCamish
Attorney, Agent, or Firm—Barnes, Kisselle, Raisch, Choate, Whittemore & Hulbert

[57] ABSTRACT

Splint material adapted for use as a splint and the like comprising a sheet of thermoplastic material which is readily formed when heated to an elevated temperature, and a layer of loop pile material bonded to one surface of the sheet such that a strap having a plurality of hooks thereon may be mechanically adhered to the loop material and released therefrom.

7 Claims, 5 Drawing Figures

SPLINT MATERIAL WITH HOOK AND LOOP FASTENER

This invention relates to splint material and particularly to thermoplastic splint material which is readily moldable when heated so that it may be formed about a limb or the like to define the splint.

BACKGROUND AND SUMMARY OF THE INVENTION

It has heretofore been proposed that a sheet of thermoplastic material be utilized to form a splint. In such a method, a sheet of thermoplastic material which can be formed about the limb or the like after it is heated is first cut to the desired pattern for the splint, then heated and formed by hand about the desired physical part. It must then be held in position until it cools, after which various fasteners or straps can be used to hold it in shape as by riveting or the like.

In such a method it is sometimes or often common to utilize two technicians, one to hold the material in place while the other forms the material to the proper shape. After the material is cooled, the straps are attached by riveting or glueing.

Among the objectives of the present invention are to provide a splint material which can be readily manipulated by one technician; wherein the splint material utilizes a fastener or strap which will hold the material in place while it cools as well as after it cools.

In accordance with the invention, the splint material adapted for use as a splint and the like comprises a sheet of thermoplastic material which is readily formed when the plastic is heated to an elevated temperature, and a layer of loop pile material bonded to one surface of the sheet such that a strap having a plurality of hooks thereon may be mechanically adhered to the loop material and released therefrom.

DESCRIPTION

Figure 1:
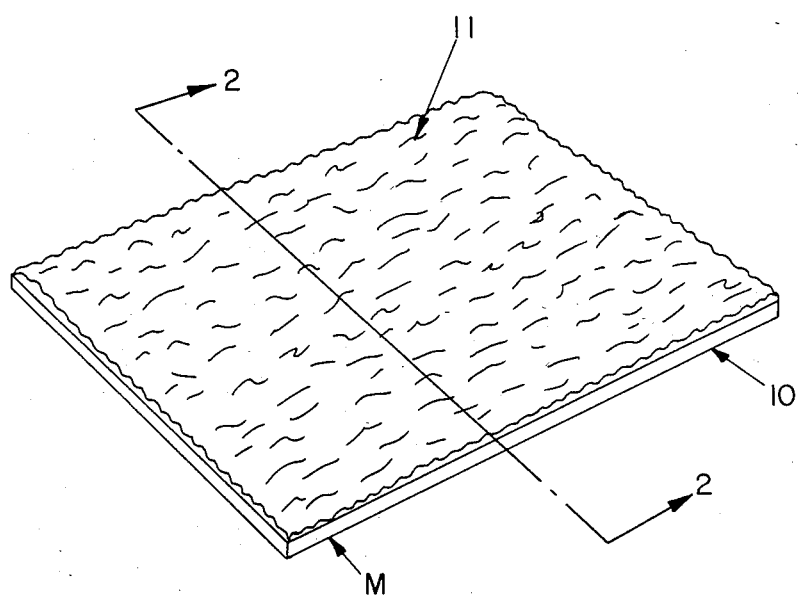
FIG. 1 is a perspective view of a splint material embodying the invention.
Figure 2:
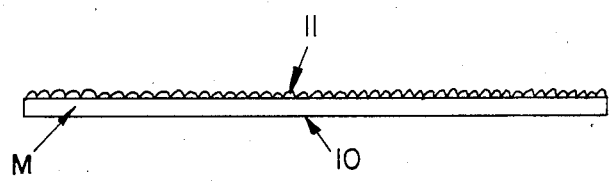
FIG. 2 is a fragmentary cross sectional view on an enlarged scale of the sheet material shown in FIG. 1.

Referring to FIGS. 1 and 2, the splint material (M) embodying the invention comprises a sheet 10 of plastic material having a layer 11 of loop material bonded to one surface thereof.

The plastic material comprises a thermoplastic material which is moldable or formable when heated to an elevated temperature, on the order of 130°–200° F., by placing in an oven, hot water or by directing hot air against the sheet. A typical thermoplastic material comprises of linear polyester. Such material is readily formed when heated, strong and retains the desired configuration upon cooling. Typical sheet material is presently made by Johnson & Johnson Products, Inc., New Brunswick, N.J., and sold under the trademark Orthoplast. Other such sheet material is sold by Rolyan Medical Products, N93 W14475 Whittaker Way, Menomonee Falls, Wis. under the trademarks Polyform, Polyflex and Ezeform. The thickness may vary but preferably is about ⅛ inch. Holes can be provided in the sheet for ventilation.

The loop pile material comprises preferably needle punch pile which consists of a plurality of fibers mechanically interconnected by what is known as a needle punch and may comprise polypropylene or polyester fibers. Typical needle punch material comprises fibers having a denier of 1.5 to 25. Alternatively, the loop material may be therammally bonded or adhered to the surface by an adhesive or bonding agent.

The invention further contemplates the use of a hook fastener strap 12 comprising a strap with a plurality of small plastic hooks 13, the hooks 13 being adapted to engage the loop pile on the surface of the plastic sheet. Such a strap is known and sold under the trademark Velcro.

Figure 3:
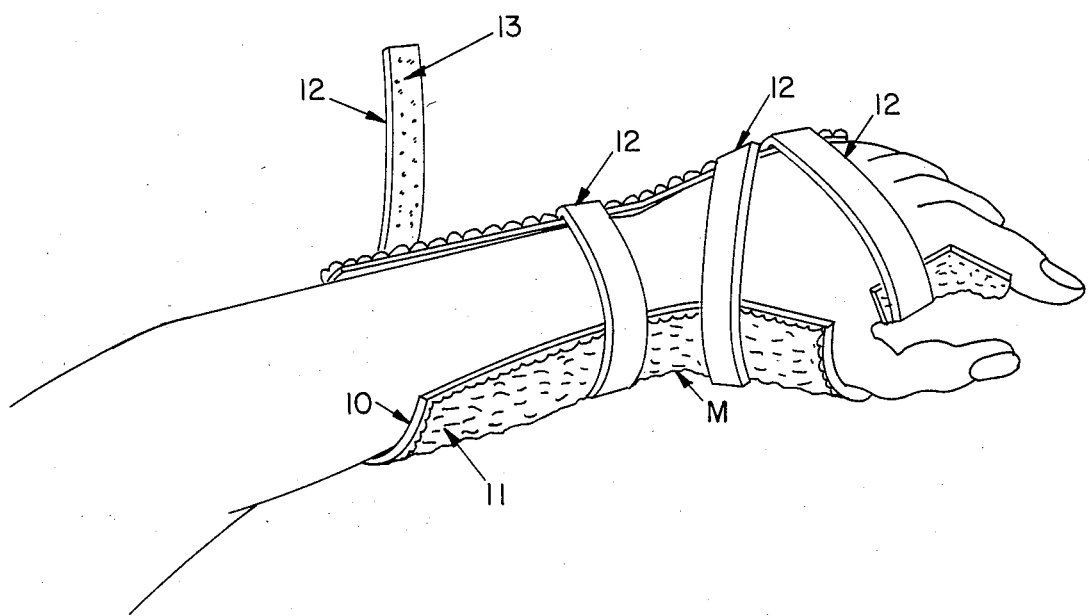
FIGS. 3, 4 and 5 are views showing the manner in which splint material embodying the invention may be utilized to form a splint.

In use, the technician cuts the sheet M to the general configuration of the splint to be formed, heats the sheet and applies it to the limb with the loop pile material 11 facing outwardly and the thermoplastic material 10 facing inwardly. The technician forms the heated sheet about the limb and then applies the straps 12 engaging the hooks 13 with the loop pile material 11, as shown for example in FIG. 3, to hold the hot splint material in position until it cools. After the material is cooled, the straps 12 can be readily readjusted if necessary.

It can thus be seen that the splint material results in a product that does not require two technicians, or the use of special fasteners such as rivets or adhesive. Inasmuch as the straps 12 hold the splint material in position, the splint may be more rapidly formed because it can be cooled more rapidly by the use of water or spray. The use of the straps 12 in connection with the layer 11 of loop material does not require precise location of the straps 12 as by use of rivets or adhesive.

Figure 4:
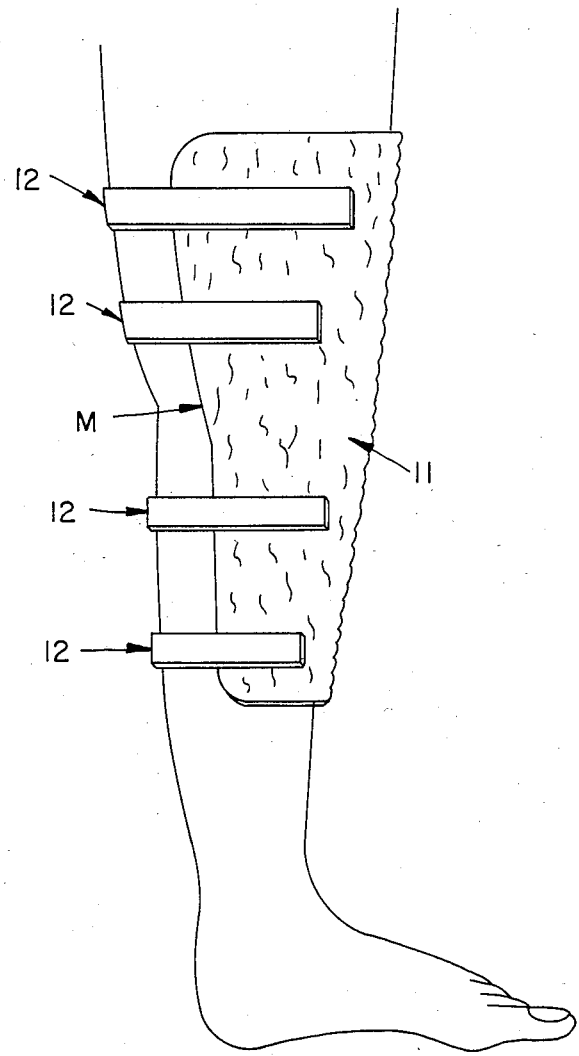
Figure 5:
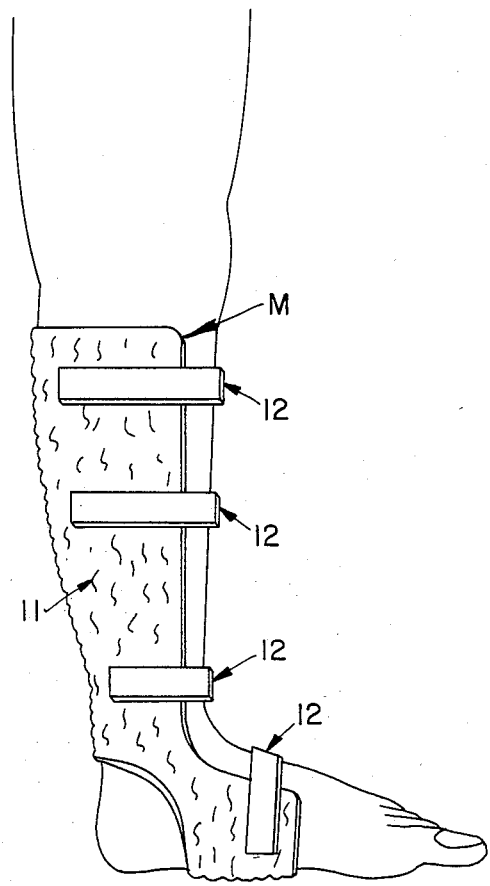

As shown in FIGS. 4 and 5, the splint material may be applied to other physical parts such as a knee (FIG. 4) or the lower leg and foot (FIG. 5).

We claim:

1. Splint material adapted for use as a splint and the like comprising
   a shape retaining sheet of thermoplastic material which is readily formed when the plastic is heated to an elevated temperature,
   and a layer of loop pile material bonded to substantially the entire surface of one face of said sheet such that the material may be cut to the desired configuration, heated, and deformed about the limb and a strap having a plurality of hooks thereon at each end thereof may be mechanically adhered to the loop material to hold the hot sheet until it is cooled and may be readily released therefrom or left in position.

2. The splint material set forth in claim 1 wherein said loop pile material extends throughout the entire surface of the sheet.

3. The splint material set forth in claim 1 wherein said loop pile material comprises a plurality of fibers interlocked to define a needle punch loop material.

4. The splint material set forth in claim 1 wherein said loop pile material is thermally bonded to the sheet.

5. The splint material set forth in claim 1 wherein said loop pile material is adhered to said sheet.

6. The splint material set forth in any of claims 1–5 including a plurality of straps, each having a plurality of closely spaced hooks on one surface thereof at each end of each strap which can be utilized to interconnect the edges of the sheet after it has been molded in place about a limb or the like by bringing the hooks into engagement with the loop pile material.

7. The method of forming a splint which comprises heating a shape retaining sheet of thermoplastic material having a loop pile material on substantially the entire surface of one face thereof to a temperature such that the plastic can be readily formed, placing the hot sheet adjacent the limb or the like about which the splint is to be made with a loop pile material facing outwardly, deforming the sheet to the desired configuration, applying a strap having a plurality of hooks at each end thereof to the opposite edges of the hot sheet encircling the limb, and permitting the plastic to cool to the desired final configuration.

* * * * *